United States Patent
Ishikura et al.

(10) Patent No.: US 8,262,685 B2
(45) Date of Patent: Sep. 11, 2012

(54) DISPOSABLE LANCING DEVICE

(75) Inventors: Kohzo Ishikura, Osaka (JP); Ken Suzuki, Osaka (JP); Takeshi Yamaguchi, Osaka (JP)

(73) Assignee: Nipro Corporation, Osaka (JP)

( * ) Notice: Subject to any disclaimer, the term of this patent is extended or adjusted under 35 U.S.C. 154(b) by 338 days.

(21) Appl. No.: 12/659,625

(22) Filed: Mar. 15, 2010

(65) Prior Publication Data
US 2010/0249819 A1 Sep. 30, 2010

(30) Foreign Application Priority Data

Mar. 27, 2009 (JP) .................. 2009-080474
Mar. 27, 2009 (JP) .................. 2009-080544

(51) Int. Cl.
*A61B 17/14* (2006.01)
*A61B 17/32* (2006.01)

(52) U.S. Cl. ................... 606/181; 606/182
(58) Field of Classification Search ......... 606/182, 606/181, 167; 600/578, 583, 584; 604/187; 215/295
See application file for complete search history.

(56) References Cited

U.S. PATENT DOCUMENTS

| | | | |
|---|---|---|---|
| 4,677,979 A | 7/1987 | Burns | |
| 4,712,548 A * | 12/1987 | Enstrom | 606/181 |
| 4,869,249 A | 9/1989 | Crossman et al. | |
| 4,895,147 A | 1/1990 | Bodicky et al. | |
| 5,324,303 A * | 6/1994 | Strong et al. | 606/181 |
| 5,385,571 A * | 1/1995 | Morita | 606/181 |
| 6,053,930 A * | 4/2000 | Ruppert | 606/181 |
| 7,223,248 B2 * | 5/2007 | Erickson et al. | 600/584 |
| 7,238,192 B2 | 7/2007 | List et al. | |
| 2002/0151920 A1 * | 10/2002 | Marshall et al. | 606/181 |
| 2004/0260324 A1 * | 12/2004 | Fukuzawa et al. | 606/181 |
| 2005/0143771 A1 * | 6/2005 | Stout et al. | 606/181 |
| 2006/0052809 A1 * | 3/2006 | Karbowniczek et al. | 606/181 |
| 2007/0135828 A1 | 6/2007 | Rutynowski | |
| 2007/0225742 A1 * | 9/2007 | Abe et al. | 606/182 |
| 2007/0293883 A1 * | 12/2007 | Horie | 606/181 |
| 2008/0058847 A1 | 3/2008 | Abe et al. | |

FOREIGN PATENT DOCUMENTS

| | | |
|---|---|---|
| DE | 197 18 081 A1 | 11/1998 |
| WO | WO 93/09723 | 5/1993 |
| WO | WO 2005/110227 A1 | 11/2005 |
| WO | WO 2006/060128 A2 | 6/2006 |

OTHER PUBLICATIONS

Extended Search Report issued in corresponding European Application No. 10002823.2, dated Jul. 6, 2010.

* cited by examiner

*Primary Examiner* — Ryan Severson
*Assistant Examiner* — Tin Nguyen
(74) *Attorney, Agent, or Firm* — Oliff & Berridge, PLC

(57) ABSTRACT

A disposable lancing device including: a housing; a spring member; a lancet having a skin puncture needle, the spring member and the lancet being housed within the housing such that a needle tip of the skin puncture needle is adapted to be projected out from the housing under urging of the lancet by the spring member to perform skin puncture procedure; and a protective cap having a needle passage hole and covering the needle tip of the skin puncture needle, the protective cap being adapted to separate from the skin puncture needle and rotate so that the needle passage hole of the protective cap is positioned on a path of projection of the skin puncture needle, and the skin puncture procedure is performed with the protective cap supported on the housing.

9 Claims, 10 Drawing Sheets

DISPOSABLE LANCING DEVICE

INCORPORATED BY REFERENCE

The disclosures of Japanese Patent Application Nos. 2009-080474 and 2009-080544 both filed on Mar. 27, 2009 and each including the specification, drawings and abstract, are incorporated herein by reference in its entirety.

BACKGROUND OF THE INVENTION

1. Field of the Invention

The present invention relates in general to a lancing device used to puncture the skin and collect a small quantity of blood, and in particular to a disposable lancing device intended to be discarded after a single use.

2. Description of the Related Art

Self-collection of small quantities of blood is sometimes necessary for medical purposes. For example, for patients with diabetes, it is necessary for the patient himself to regularly collect his own blood in order to periodically check blood sugar level (Self-Monitoring of Blood Glucose: SMBG). Lancing devices have been in use for some time to enable such self-collection of blood to be carried out safely and dependably.

Such lancing devices typically have a structure in which a spring member and a lancet having a skin puncture needle are housed within a housing. By extending the tip of the skin puncture needle out from the housing through urging of the lancet by the spring member, the skin puncture needle punctures the skin surface so that a small quantity of blood is exuded. Particularly in recent years, with a view to preventing spread of the HIV or hepatitis B virus through the agency of used skin puncture needles, lancing devices of disposable type designed to be discarded after a single use have come into widespread use.

With lancing devices of this kind, the skin puncture needle is covered beforehand by a resin protective cap in order to maintain the skin puncture needle in a sterile condition until use. Specific examples of lancing devices furnished with such a protective cap are disclosed inter alia in US Patent Application Publication NO. US-A-2007/135828, International Publication No. WO2005/110227, and International Publication WO2006/060128. Such a protective cap must first be detached from the lancing device, e.g. by twisting and breaking it off prior to use, and considerable inconvenience is associated with the need to detach the cap and dispose of the detached cap.

SUMMARY OF THE INVENTION

It is therefore one object of this invention to provide a disposable lancing device of novel construction which does not require that a protective cap covering the skin puncture needle be detached from the housing.

The above and/or optional objects of this invention may be attained according to at least one of the following modes of the invention. The following modes and/or elements employed in each mode of the invention may be adopted at any possible optional combinations. It is to be understood that the principle of the invention is not limited to these modes of the invention and combinations of the technical features, but may otherwise be recognized based on the teachings of the present invention disclosed in the entire specification and drawings or that may be recognized by those skilled in the art in the light of the present disclosure in its entirety.

One mode of the present invention provides a disposable lancing device including: a housing; a spring member; a lancet having a skin puncture needle, the spring member and the lancet being housed within the housing such that a needle tip of the skin puncture needle is adapted to be projected out from the housing under urging of the lancet by the spring member to perform skin puncture procedure; and a protective cap having a needle passage hole and covering the needle tip of the skin puncture needle, the protective cap being adapted to separate from the skin puncture needle and rotate so that the needle passage hole of the protective cap is positioned on a path of projection of the skin puncture needle, and the skin puncture procedure is performed with the protective cap supported on the housing.

According to the present invention, there is no need for the protective cap covering the skin puncture needle to be detached from the housing, thus eliminating the inconvenience of disposing of the detached cap.

In accordance with another preferred mode of the present invention, the protective cap has a cap body in which the needle passage hole has been formed, and support shafts provided to the cap body and extending perpendicular to the direction of passage of the needle passage hole; while the housing is provided with support grooves extending in the direction of extension of the skin puncture needle, with the support shafts of the protective cap being supported in the support grooves of the housing.

With this arrangement, by rotating the support shafts of the protective cap which are supported in the support grooves, the protective cap body will rotate as well, making it possible to easily position the needle passage hole of the protective cap on the projection path of the skin puncture needle.

In accordance with yet another preferred mode of the present invention employed concomitantly with the preceding mode, the support shafts of the protective cap are provided with projecting guide pieces that extend in the direction of passage of the needle passage hole; the support grooves of the housing have a wide-width part, a narrow-width part, and a sloping part that connects the wide-width part with the narrow-width part; and the protective cap is designed to be rotated by sliding the projecting guide pieces into the support grooves and movement thereof from the wide-width part end towards the narrow-width part end.

According to this mode, the protective cap can be rotated automatically through a simple procedure of the protective cap moving along the support grooves which have been provided to the housing.

In accordance with yet another preferred mode of the present invention, during the skin puncture procedure, the protective cap which has separated from the skin puncture needle defines a stopper part against which the lancet comes into abutment; and the degree of extension of the skin puncture needle beyond the housing is adjustable through modification of a position of a traveling end of the lancet in a direction of projection of the skin puncture needle, which is regulated by abutment thereof against the stopper part.

According to this mode, the protective cap which protects the needle tip of the skin puncture needle defines a stopper part against which the lancet comes into abutment. With this arrangement, through a simple design having few parts, safety through protection of the skin puncture needle tip can be achieved concomitantly with a mechanism for adjusting the puncture depth of the skin puncture needle. Lower production cost and smaller size of the disposable lancing device can be achieved as well.

In the present mode in particular, with regard to the two independent elements of the "skin puncture needle protective cap" and the "lancet stopper" which are completely unrelated to one another in purpose and action, by envisioning a novel particular relationship between both elements, assurance of safety by virtue of protecting the skin puncture needle tip is achieved concomitantly with a mechanism for adjusting skin puncture needle puncture depth, in a simple design having few parts. Specifically, as disclosed respectively in US Patent Application Publication NO. US-A-2007/225742 and U.S. Pat. No. 4,895,147, in conventional practice, the protective cap and the stopper were merely provided as mutually unrelated separate structures for attaining completely different objectives. However, the inventors noted the existence of a relationship between the protective cap and the stopper whereby the functionality of the former is needed only prior to the skin puncture procedure, whereas that of the latter is needed only during the skin puncture procedure. That is, the stopper is nonfunctional and unneeded at times that the functionality of the protective cap is needed, while conversely the protective cap is nonfunctional and unneeded at times that the functionality of the stopper is needed. The present mode was perfected by discovering and then building upon this particular relationship between the protective cap and the stopper, which two elements in conventional practice were not viewed as anything other than two completely independent arrangements. Thus, according to the present mode, on the basis of the novel inventive step whereby the protective cap, whose function is needed prior to the skin puncture procedure, will be skillfully utilized to provide the stopper during the skin puncture procedure, at which time its function is unneeded, skin puncture needle protection functionality and skin puncture needle projection adjustment functionality during puncture are realized through a simple construction with shared parts.

In the present mode, an arrangement for modifying the position of the traveling end of the lancet in the direction of extension of the skin puncture needle may be accomplished, for example, through displacement of the location of the abutting faces of the lancet and the stopper part with respect to the housing in the direction of skin puncture needle projection. More specifically, by designing at least one of the abutting face on the lancet side and the abutting face on the stopper side to be adjustable in the direction of skin puncture needle projection, it will be possible to modify the position of the traveling end of the lancet in the direction of skin puncture needle projection.

According to another possible mode in the present invention, the housing includes a pressing member adapted to be pressed against a skin surface at a blood collection site, and an operating member moveably linked to the pressing member; and the operating member is movable to release a locked state of the lancet urged by the spring member with respect to the pressing member so that the skin puncture procedure is carried out by projecting the skin puncture needle out from the pressing member.

With such an arrangement, the skin puncture procedure can be carried out by releasing the lancet from the locked state through movement of the operating member with respect to the pressing member. For this reason it is also possible to carry out the skin puncture procedure with one hand while holding the operating member, providing superior ease of operation.

In accordance with yet another preferred mode of the present invention employed concomitantly with the above mode, wherein both the pressing member and the operating member are of tubular shape having a bottom, and are oriented with openings thereof fitting together and assembled so as to be capable of relative movement in an axial direction to produce a hollow structure for the housing; the lancet is accommodated in the housing so as to be moveable in the axial direction thereof, with the skin puncture needle of the lancet projecting towards a base part of the pressing member and with a puncture opening formed in the base part of the pressing member; the protective cap is designed to separate from the skin puncture needle and to rotate through push operation of the operating member against the pressing member with the base part of the pressing member being pressed against the skin surface at the blood collection site; and the skin puncture procedure is carried out by releasing the lancet from the locked state with respect to the pressing member, whereupon the lancet moves towards the base part of the pressing member under urging force of the spring member situated between the housing and the lancet, causing the needle tip of the skin puncture needle to project to an outside through the puncture opening of the pressing member to carry out the skin puncture procedure.

According to the present mode, with the pressing member pressed against the skin surface, the skin puncture procedure can be effected through a simple operation of pushing in the operating member towards the skin surface with respect to the pressing member. During the skin puncture procedure, the pressing member is prevented from separating from the skin surface, so consistent puncture depth may be achieved.

In yet another preferred mode in which the housing includes the pressing member and the operating member, the operating member is furnished with a safety lock mechanism adapted to arrest operation for releasing the locked state of the lancet urged by the spring member with respect to the pressing member. By providing a safety lock mechanism, it is possible to prevent the cap from detaching and the needle tip of the skin puncture needle from sticking out if the pressing member is inadvertently pushed, thus avoiding accidental needlesticks.

In yet another preferred mode in which the housing includes the pressing member and the operating member, when the protective cap which is supported by the pressing member and the lancet which is supported by the operating member experience relative rotation through coaxial relative rotation of the pressing member with respect to the operating member, the location at which the lancet comes into abutment with the stopper part formed on the protective cap changes so as to produce an associated change in a position of a traveling end of the lancet which is regulated by abutment thereof against the stopper part.

In the present mode, since adjustment of the degree of extension of the skin puncture needle can be carried out through relative rotation of the pressing member and the operating member which make up the principal components of the housing, it is possible to give the device a simple appearance and make it easy to operate. Moreover, by adopting relative rotation as the direction of operation of the pushing member and the operating member during adjustment of the degree of extension of the skin puncture needle, this operation can be distinguished from the operation of the pushing member and the operating member during the skin puncture procedure with the skin puncture needle, so that the two operations can be performed dependably without confusion.

In yet another preferred mode in the present invention, a position of an abutting face of the stopper part which abuts the lancet is changeable in the direction of extension of the skin puncture needle. This change in position of the abutting face may be made adjustable in stepwise fashion by designing the abutting face to have multiple stepped faces in the skin puncture needle projection direction; or the position of the stopper part may be made adjustable in stepless fashion in the skin puncture needle projection direction through a screw feed mechanism or the like.

In yet another preferred mode in which the operating member is employed, the device further includes an interlock mechanism whereby operating force exerted on the operating member during the skin puncture procedure is transmitted to the protective cap so that the protective cap is induced to separate from the skin puncture needle and is guided to a location for constituting the stopper part. With this arrangement, separation of the protective cap from the skin puncture needle and formation of the stopper part can take place automatically by utilizing operating force during the skin puncture procedure, making it possible for the series of steps of the skin puncture procedure inclusive of separation of the protective cap and formation of the stopper part can be carried out more easily and quickly.

According to the present invention, there is no need to detach the protective cap covering the skin puncture needle from the housing.

BRIEF DESCRIPTION OF THE DRAWINGS

The foregoing and/or other objects features and advantages of the invention will become more apparent from the following description of a preferred embodiment with reference to the accompanying drawings in which like reference numerals designate like elements and wherein.

DETAILED DESCRIPTION OF PREFERRED EMBODIMENTS

Figure 1:
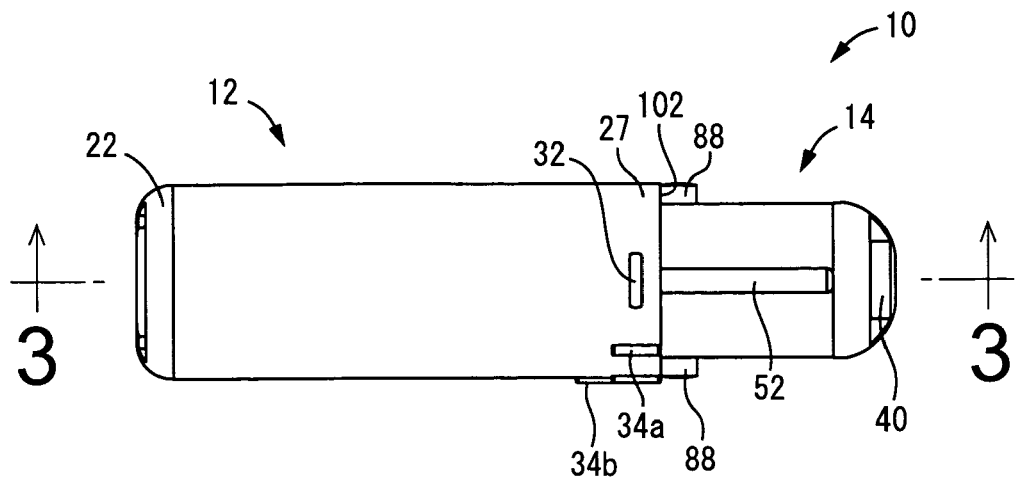
FIG. 1 is a side view of a disposable lancing device according to one embodiment of the present invention.
Figure 2:
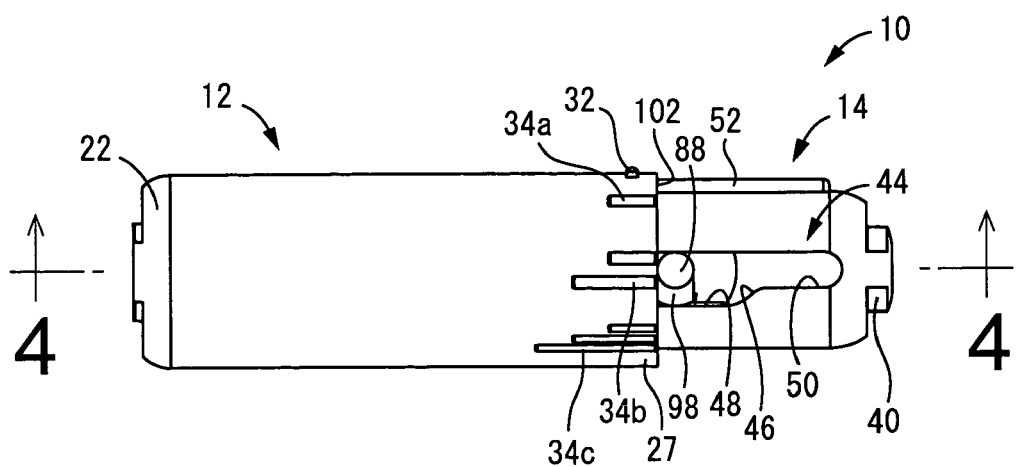
FIG. 2 is another side view of the disposable lancing device of FIG. 1.
Figure 3:
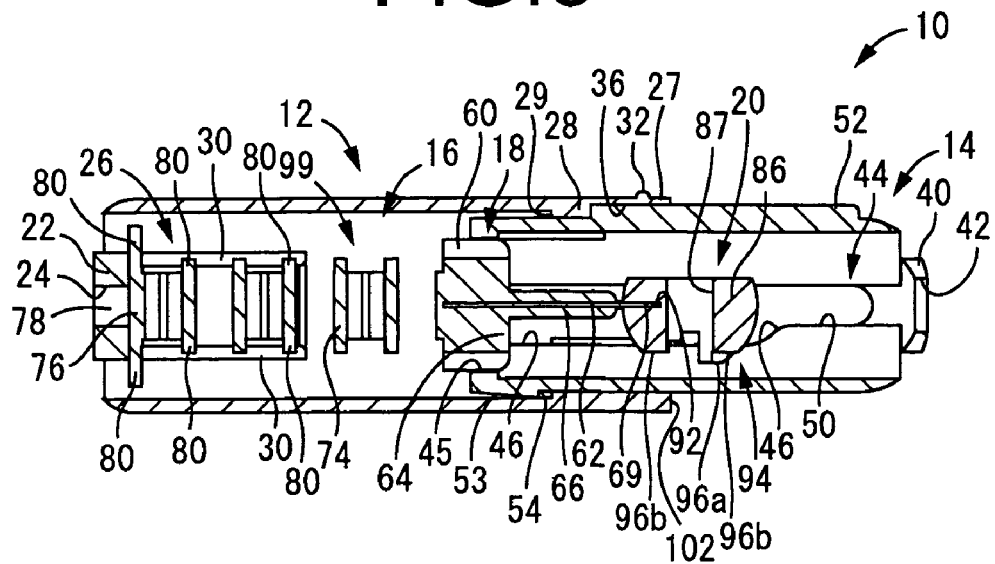
FIG. 3 is a cross sectional view taken along line 3-3 of FIG. 1.
Figure 4:
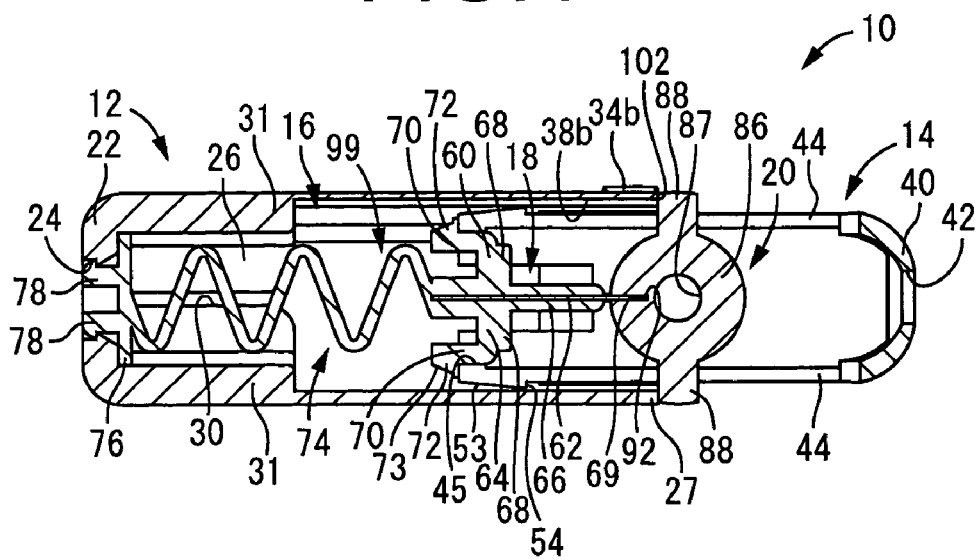
FIG. 4 is a cross sectional view taken along line 4-4 of FIG. 2.
Figure 5:
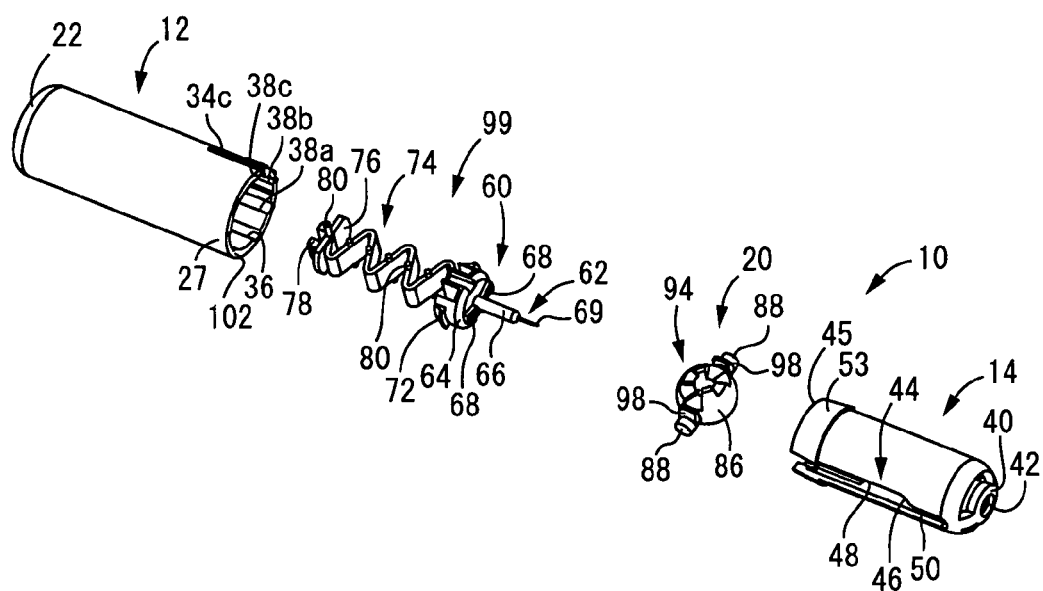
FIG. 5 is an exploded perspective view of the disposable lancing device of FIG. 1.

First, FIGS. 1 to 5 depict a disposable lancing device (hereinafter termed simply "lancing device" for convenience) 10 according to one embodiment of the present invention. The lancing device 10 is furnished with a housing 16 assembled from an operating member 12 and a pressing member 14; a lancet 18 and a protective cap 20 are housed in this housing 16. In the following description, unless indicated otherwise, front refers to the right side in FIG. 1, back refers to the left side in FIG. 1, and axial direction refers to the left-right direction in FIG. 1.

Turning to a more detailed discussion, the operating member 12 is of bottomed, approximately round tubular shape. A mating hole 24 is formed extending through the center section of its base part 22 in the axial direction.

A housing tube portion 26 that projects axially inward from the base part 22 has been integrally formed in the interior of the operating member 12. The mating hole 24 of the base part 22 opens into the back end part of this housing tube portion 26. Meanwhile, the front end part of the housing tube portion 26 opens into the operating member 12.

At the end of the operating member 12 on an opening 27 side thereof there is disposed a catch projection 28 that projects up from the inner circumferential face and extends in the circumferential direction. The edge face of this catch projection 28 on the axially inward side thereof defines a detent step face 29 that projects up from the inner circumferential face of the operating member 12.

In the housing tube portion 26 there are additionally formed a pair of insertion grooves 30, 30 of slit shape situated in the peripheral wall section. This pair of slit-shaped insertion grooves 30, 30 extend in the axial direction of the housing tube portion 26 and lie open at the distal end of the housing tube portion 26. In localized sections along its circumference the housing tube portion 26 has thick-walled construction integral with the peripheral wall of the operating member 12. Specifically, a pair of linking portions 31, 31 that integrally link the housing tube portion 26 with the peripheral wall of the operating member 12 are formed between the two in localized sections on the circumference. The direction of opposition of the pair of insertion grooves 30, 30 and the direction of opposition of the linking portions 31, 31 are both axis-perpendicular to the housing tube portion 26, as well as orthogonal to one another.

A plurality of indicia 32, 34a, 34b, 34c defined by raised projections have been formed on the outside peripheral face of the operating member 12. One of these, an initial stage indicia 32, is disposed in proximity to the rim on the opening 27 side, and is intended to indicate the initial stage rotation position of the pressing member 14 with respect to the operating member 12, discussed later. A first indicia 34a, a second indicia 34b, and a third indicia 34c are provided for the purpose of selective setting of the degree of extension of a skin puncture needle 62, discussed later, and are defined by linear raised projections extending in the axial direction from the rim at the opening 27 side of the operating member 12.

The first indicia 34a is composed of a single linear raised projection, the second indicia 34b is composed of two linear raised projections, and the third indicia 34c is composed of three linear raised projections to distinguish them from one another. In particular, the linear raised projections have progressively greater length going from the first indicia 34a to the second indicia 34b and then to the third indicia 34c, providing a visual representation of the progressively greater settings of the degree of extension of the skin puncture needle 62. The initial stage indicia 32 and the first to third indicia 34a, 34b, 34c are disposed at approximately unchanging intervals in the circumferential direction of the operating member 12.

Figure 6:
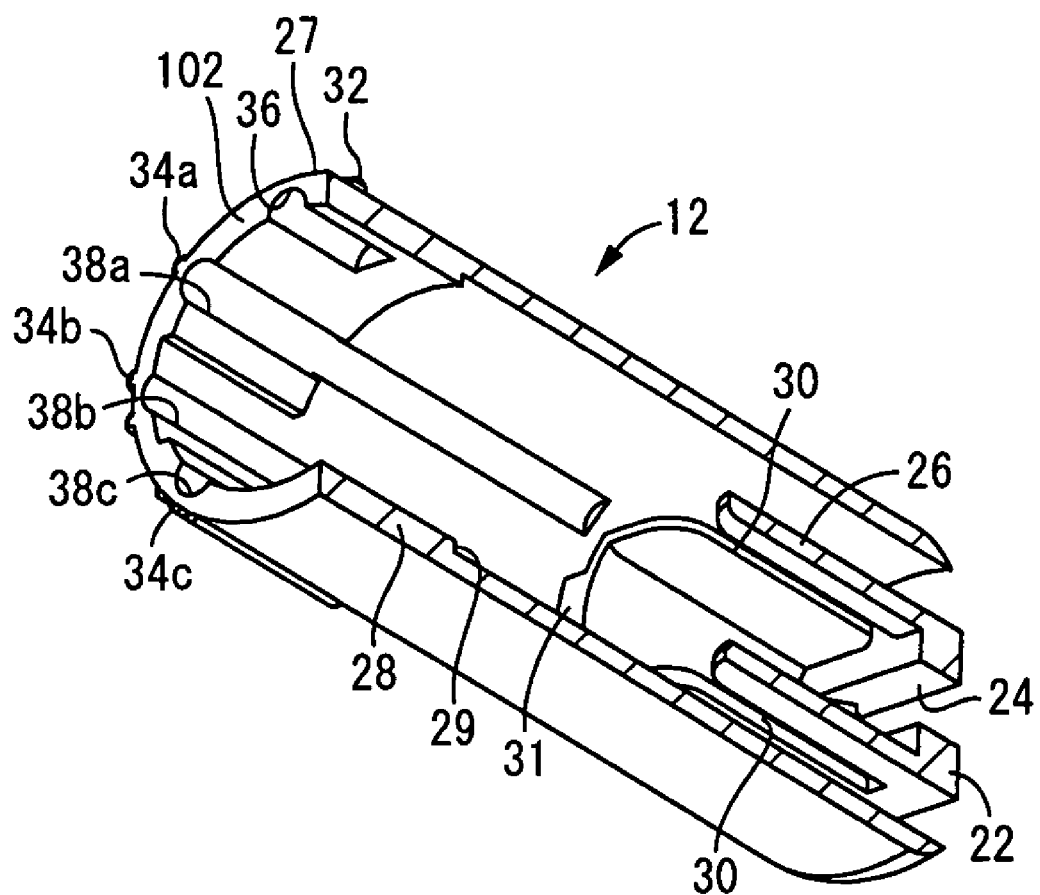
FIG. 6 is a perspective view in cross section of an operating member of the disposable lancing device of FIG. 1.

As depicted in FIG. 6, a plurality of grooves 36, 38a, 38b, 38c have been formed on the inside peripheral face of the operating member 12. These grooves 36, 38a, 38b, 38c are all constituted by recesses which extend in the axial direction from the rim at the opening 27 side of the operating member 12. One of these, an initial stage mating groove 36, is located at the inside peripheral face of the initial stage indicia 32. A first guide groove 38a is located at the inside peripheral face of the first indicia 34a, a second guide groove 38b is located at the inside peripheral face of the second indicia 34b, and a third guide groove 38c is located at the inside peripheral face of the third indicia 34c.

The first to third guide grooves 38a-38c are approximately equal in axial length, and extend into proximity with the open end of the housing tube portion 26 inside the operating member 12. The initial stage mating groove 36, on the other hand, is shorter than the first to third guide grooves 38a-38c.

Meanwhile, the pressing member 14 is of bottomed, approximately round tubular shape. The outside diameter dimension of its tube wall permits it to be slipped inside the operating member 12. A puncture opening 42 is formed extending through the center section in a base part 40 of the pressing member 14.

A pair of support grooves 44, 44 have been formed in the tube wall of the pressing member 14. Each support groove 44 is of slit form extending through the tube wall and leading in the axial direction from the end of the pressing member 14 on an opening 45 side thereof and into proximity with its base part 40. The width dimension of each support groove 44 varies in the medial section in the lengthwise direction. Specifically, a sloping part 46 is provided in the lengthwise medial section of one of the side walls of each support groove 44, with the side lying towards the opening 45 from this sloping part 46 constituting a wide-width part 48, and the side lying towards the base part 40 from this sloping part 46 constituting a narrow-width part 50.

The pair of support grooves 44, 44 have been formed at locations in opposition across the diameter of the tube wall of the pressing member 14. The sloping parts 46, 46 of the pair of support grooves 44, 44 appear to overlap one another in side view of the pressing member 14 (see FIG. 2).

A raised rib 52 has been formed on the outside peripheral face of the pressing member 14, and extends in the axial direction through the circumferential medial section of the pair of support grooves 44, 44. As discussed later, this rib 52, in cooperation with the indicia 32, 34a, 34b, 34c of the operating member 12, functions to indicate operational status of the lancing device 10.

The pressing member 14 is provided at the end thereof on the opening side with a thick-walled part having large outside diameter dimension. The outside peripheral face of this thick-walled part constitutes a tapered face 53 of progressively smaller diameter towards the opening 45 side. The axial end face on the large-diameter side of the thick-walled part constitutes a locking step face 54 that projects up from the outside peripheral face of the pressing member 14.

This tapered face 53 facilitates insertion of the pressing member 14 into the operating member 12. During insertion, once the tapered face 53 of the pressing member 14 has passed beyond the catch projection 28 of the operating member 12, the locking step face 54 of the pressing member 14 will become detained by the detent step face 29 of the operating member 12, thus preventing the pressing member 14 from becoming dislodged from the operating member 12.

Meanwhile, the lancet 18 includes a lancet hub 60 and the skin puncture needle 62. The lancet hub 60 is made of synthetic resin such as polypropylene, polyethylene, polycarbonate, ABS resin, or acrylic resin, and has a circular disk part 64 and a needle retention part 66 of cylindrical shape projected along the center axis of the circular disk part 64. On the projecting face of the needle retention part 66 of the circular disk part 64, a pair of abutting parts 68, 68 have been integrally formed. The pair of abutting parts 68, 68 project out respectively in fan shapes which are symmetrical in the diametrical direction of the circular disk part 64. The basal section of the skin puncture needle 62 is secured to the needle retention part 66 of the lancet hub 60 through insert molding, adhesive bonding, or the like, and a needle tip 69 of the skin puncture needle 62 extends outwardly along the center axis of the lancet hub 60.

A pair of outside peripheral walls 70, 70 have been formed in the outside peripheral section of the circular disk part 64, and are projected in the opposite axial direction from the needle retention part 66 of the circular disk part 64. A catch claw 72 has been formed on the outside peripheral face of each peripheral wall 70. The outside peripheral face of the catch claw 72 constitutes a tapered face 73 with progressively expanding diameter towards the direction of extension of the skin puncture needle 62.

A spring member 74 has been integrally formed with the circular disk part 64. In the present embodiment, the spring member 74 is constituted by a plate spring made of resin having an accordion-like convoluted shape, one end of which has been linked to the circular disk part 64. The spring member 74 projects out from the circular disk part 64 in the opposite axial direction from the needle retention part 66. A mounting plate part 76 has been integrally formed at the other end of the spring member 74. A pair of mating claws 78, 78 are disposed on the mounting plate part 76, on the face thereof on the opposite side from the spring member 74.

A plurality of insertion pins 80 that project out to both sides in the width direction have been formed on the spring member 74 and the mounting plate part 76. These insertion pins 80 have all been projected out on straight lines extending in the width direction of the spring member 74 and the mounting plate part 76 and intersecting the centerline of the circular disk part 64. The projecting dimension of the insertion pins 80 formed on the mounting plate part 76 is greater than the projecting dimension of the insertion pins 80 formed on the spring member 74. The insertion pins 80 have been arranged aligned on a straight line that extends along the direction of convolution of the spring member 74, through the medial sections which are situated between the peaks and valleys of the accordion-like convoluted shape of the spring member 74.

Figure 7:
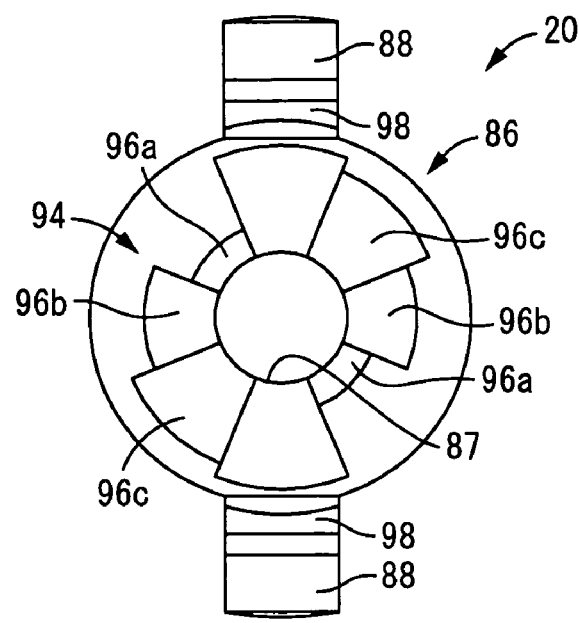
FIG. 7 is a front view of a protective cap of the disposable lancing device of FIG. 1.
Figure 8:
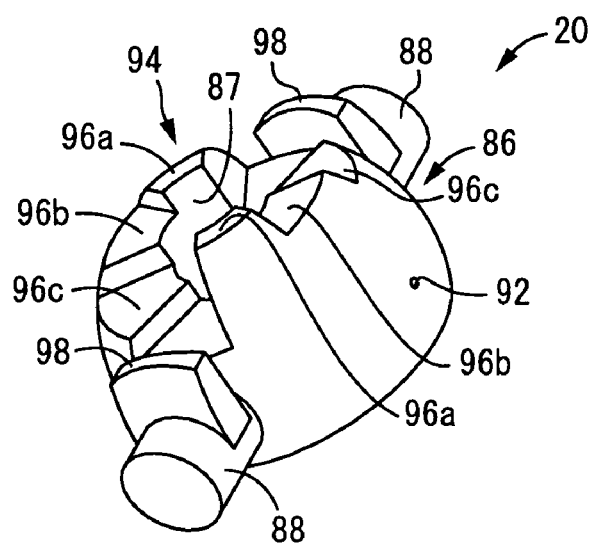
FIG. 8 is a perspective view of the protective cap of FIG. 7.

As depicted in FIGS. 7 and 8, the protective cap 20 is furnished with a cap body 86 of thick-walled, approximately round tubular shape (with approximately semispherical shape the inside diameter dimension of which is generally unchanging along the entire length, while the outside diameter dimension varies along an axis in the axial direction). A center hole of this cap body 86 defines a needle passage hole 87. The outside peripheral face of the cap body 86 becomes progressively smaller in diameter from first axial end towards the other axial end, producing a curved outside peripheral face of approximately semispherical shape. Additionally, a pair of support shafts 88, 88 that project out in the axis-perpendicular direction have been integrally formed at the large-diameter end of the cap body 86. A needle storage hole 92 has been formed in the outside peripheral face of the cap body 86 in proximity to its large-diameter end, and extends in the orthogonal direction to the projecting direction of the pair of support shafts 88, 88, for a distance not far enough to reach the needle passage hole 87. That is, in the protective cap 20, the support shafts 88, 88, the needle passage hole 87, and the needle storage hole 92 extend in three different orthogonal directions.

A stopper part 94 has been formed on the axial end face at the small-diameter end of the cap body 86. The stopper part 94 is defined by first to third stopper faces 96a, 96b, 96c that project in the axial direction of the cap body 86. These first to third stopper faces 96a, 96b, 96c are respectively formed by the distal end faces of a pair of fan-shaped projections situated in opposition in the diametrical direction of the cap body 86, viewed in the direction of the axis of the needle passage hole 87. In the present embodiment, the first to third stopper faces 96a, 96b, 96c are each constituted as fan shapes with a central angle of approximately 45°. The first to third stopper faces 96a, 96b, 96c differ from one another in their projected height outward in the axial direction of the cap body 86, with the first stopper face 96a, the second stopper face 96b, and the third stopper face 96c having progressively smaller projected dimensions, in that order.

The pair of support shafts 88, 88 have outside diameter dimension permitting them to slide through the narrow-width part 50 of the support grooves 44, 44 of the pressing member 14. A projecting guide piece 98 is formed in a zone of the support shaft 88 lying towards the cap body 86 side and projects towards the stopper part 94 side of each support shaft 88. The projected height of the projecting guide pieces 98 has been established such that, with their direction of projection aligned with the widthwise direction of the support grooves 44 of the pressing member 14, it is possible for the support shafts 88 insert into the wide-width part 48 of the support grooves 44, but not to insert into the narrow-width part 50.

Ordinarily, the protective cap 20 may be integrally molded with the lancet 18 through an insert molding process using a mold cavity in which the skin puncture needle 62 has been arranged. By so doing, the needle tip 69 of the skin puncture needle 62 will be protected by the protective cap 20, and the needle storage hole 92 discussed earlier will be formed in the protective cap 20.

A lancet structure 99 constituted by attaching the skin puncture needle 62 to the needle retention part 66 of the lancet 18 is slipped into the housing tube portion 26 of the operating member 12, and the mating claws 78 are mated with the mating hole 24 of the operating member 12. The lancet structure 99 is thereby attached to the operating member 12 with the mounting plate part 76 secured juxtaposed against the inside face of the base part 22 of the operating member 12. The insertion pins 80 which have been projected from the spring member 74 are passed through the insertion grooves 30 of the housing tube portion 26. This arrangement permits extensional and contractive elastic deformation of the spring member 74 while preventing it from tilting so as to more consistently produce the intended elastic deformation.

The protective cap 20 may be integrally formed with the lancet 18 by insert molding as described above, or formed separately from the lancet 18. In the latter instance, installation of the protective cap 20 onto the skin puncture needle 62 may be carried out prior to attachment of the lancet structure 99 to the operating member 12, or after attachment. During installation of the protective cap 20 onto the skin puncture needle 62, in order to maintain the sterile conditions discussed later, it is preferable to slip it on until the distal end of the needle retention part 66 which retains the skin puncture needle 62 inserts into the needle storage hole 92 of the protective cap 20.

The pressing member 14 is then attached to the operating member 12 by being fitted therein through the opening. During this process, the support shafts 88 of the protective cap 20 will intrude into the support grooves 44 of the pressing member 14. The pressing member 14 is then pushed into the operating member 12 until the tapered face 53 of the pressing member 14 is positioned axially to the back of the detent step face 29 of the operating member 12. By so doing, the locking step face 54 of the pressing member 14 will become locked by the detent step face 29, and the pressing member 14 will be attached in a condition of being positioned concentrically with the operating member 12 and fitting therein nondetachably.

The lancet structure 99 and the protective cap 20 are housed inside the housing 16 of the lancing device 10 which has been assembled in this way. In the assembled state, the needle tip 69 of the skin puncture needle 62 will face towards the base part 40 of the pressing member 14, while the spring member 74 will be positioned between the lancet 18 and the base part 22 of the operating member 12.

The lancing device 10 then undergoes treatment so that at a minimum the needle tip 69 of the skin puncture needle 62 and the cap body 86 protecting it are placed in a sterile condition. As a specific example, the skin puncture needle 62, either prior to or after installing the cap body 86, may be subjected to a sterilization process through radiation, high-pressure steam sterilization, or the like. By integrally molding the lancet 18 and the protective cap 20 using a mold cavity in which the skin puncture needle 62 has been arranged, the needle tip 69 of the skin puncture needle 62 can be kept in a sterile condition.

The operating member 12 and the pressing member 14 are assembled rotatably with respect to one another about a common center axis. In the present embodiment, as depicted in FIGS. 1 to 4, the lancing device 10 is provided to the user in an initial condition with the rib 52 of the pressing member 14 positioned aligned with the initial stage indicia 32 in the circumferential direction of the operating member 12, and mated with the initial stage mating groove 36.

In this initial state, the protective cap 20 is accommodated with the support shafts 88 and the projecting guide pieces 98 inserted into the wide-width part 48 of the support grooves 44 of the pressing member 14, and with the projection direction of the projecting guide pieces 98 oriented in a direction orthogonal (the vertical direction in FIG. 2) to the direction of extension of the support grooves 44. The projecting guide pieces 98 are positioned within the wide-width part 48 with their projecting distal edge lying towards the sloping part 46 side from the support shaft 88. Thus, the protective cap 20 will be positioned with the needle storage hole 92 situated to the skin puncture needle 62 side with respect to the support shafts 88 and extending along the center axis of the pressing member 14. The section of the skin puncture needle 62 that projects out from the needle retention part 66 has been inserted into the needle storage hole 92 so that the needle tip 69 is protected by the protective cap 20 by virtue of being positioned inside the needle storage hole 92.

In this initial state, the axial back edge face of the rib 52 is detained at the axial back edge face of the initial stage mating groove 36, thereby preventing the operating member 12 from being pushed the axial direction with respect to the pressing member 14, and providing a safety lock mechanism composed of the rib 52 and the initial stage mating groove 36.

Figure 9A:
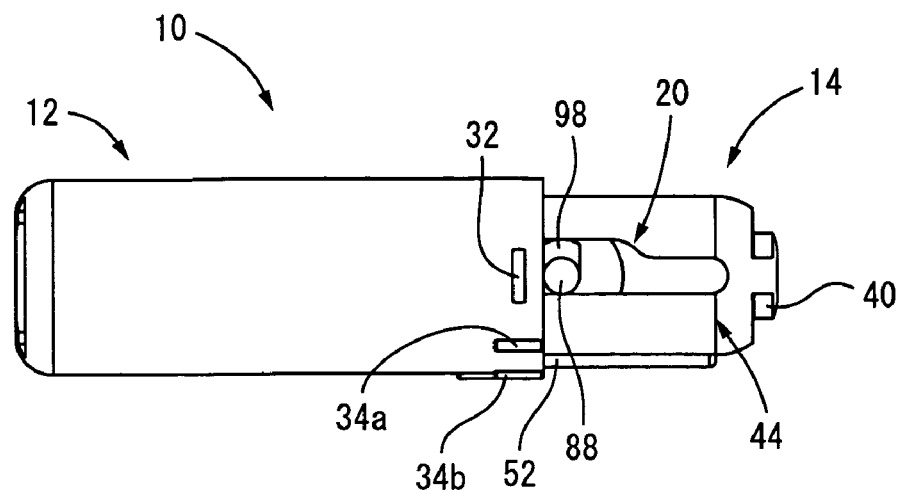
FIGS. 9A and 9B are views for explaining one step of a skin puncture procedure by the disposable lancing device, wherein a safety lock mechanism is released through coaxial relative rotation of a pressing member with respect to an operating member.
Figure 9B:
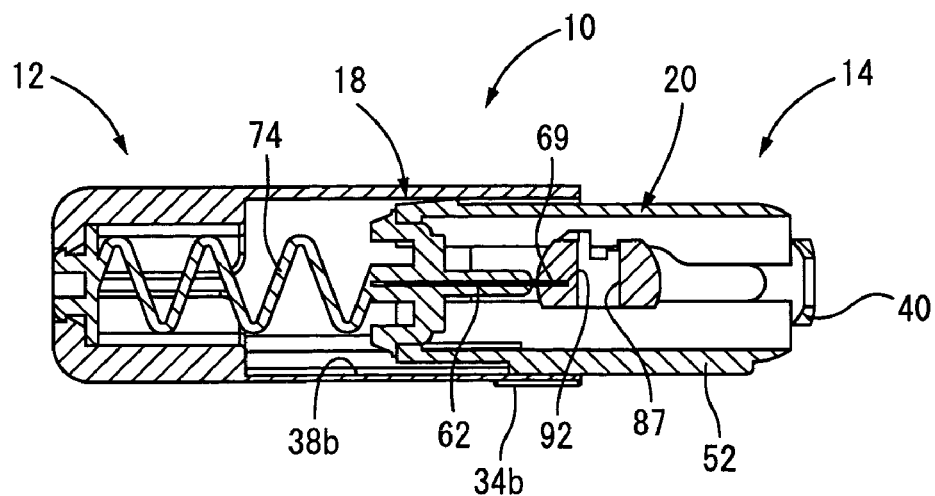

In the lancing device 10 constructed in this way, because the support grooves 44 of the pressing member 14 have been formed with notched shape open at the axial back end of the pressing member 14, a slight degree of deformation in the diameter constriction direction is possible at the axial back end of the pressing member 14, thereby permitting the pressing member 14 to rotate about the center axis with respect to the operating member 12. During use of the lancing device 10, as depicted in FIGS. 9A and 9B, first, the pressing member 14 is rotated about the center axis with respect to the operating member 12 until the rib 52 is aligned with a desired indicia selected from the first to third indicia 34a, 34b, 34c, so that the rib 52 mates with one of the first to third guide grooves 38a, 38b, 38c. In FIGS. 9A and 9B, the rib 52 is depicted as being aligned with the second indicia 34b and mating with the second guide groove 38b.

Through this rotation procedure, the protective cap 20, together with the pressing member 14, rotate about the center axis with respect to the lancet 18. Because the first to third guide grooves 38a, 38b, 38c extend further towards the back in the axial direction of the operating member 12 than does the initial stage mating groove 36 which has been formed at the location of the initial stage indicia 32, with the rib 52 mated with any of the first to third guide grooves 38a, 38b, 38c, the operating member 12 will be permitted to undergo relative displacement in the axial direction with respect to the pressing member 14.

Figure 10A:
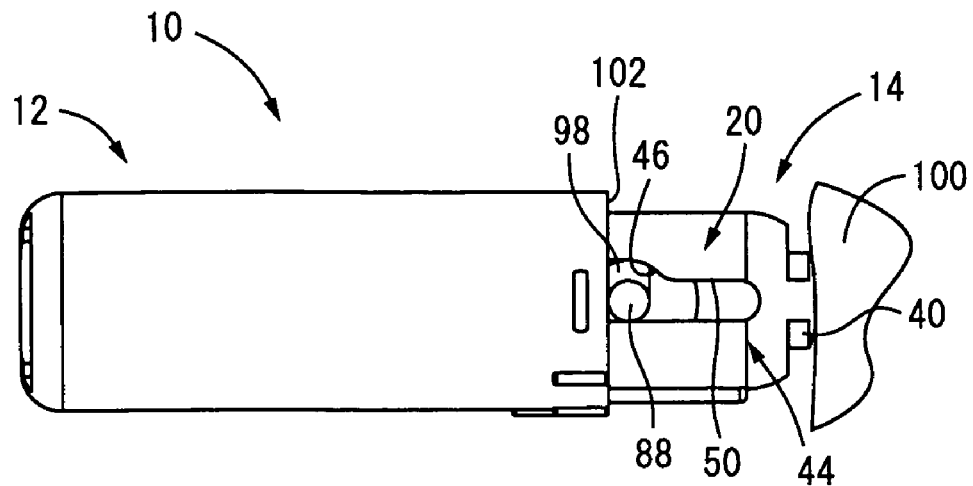
FIGS. 10A and 10B are views for explaining the following step of the skin puncture procedure of FIGS. 9A and 9B, wherein a skin puncture needle is released from the protective cap within a housing.
Figure 10B:
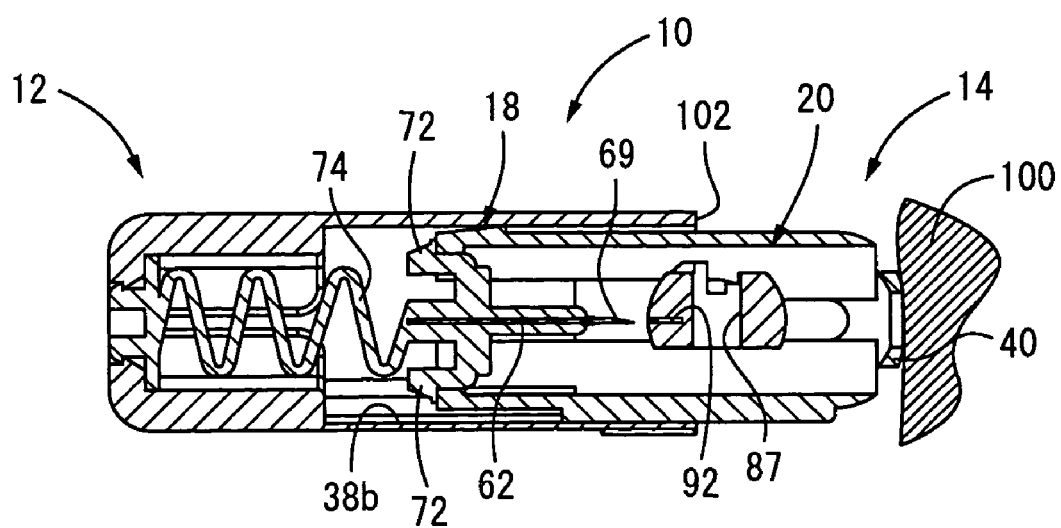

Next, as depicted in FIGS. 10A and 10B, the base part 40 of the pressing member 14 is pressed against a skin surface 100 at the collection site (depicted in model form) while pushing the operating member 12 towards the pressing member 14 in the axial direction. At this point, with the support shafts 88 respectively projecting outward from the support grooves 44 of the pressing member 14 in the diametrical direction of the pressing member 14, the protective cap 20 will be subjected to pushing force from the operating member 12 by virtue of being in abutment with a rim face 102 of the operating member 12, and will travel towards the front in the axial direction of the pressing member 14. Meanwhile, as regards the lancet 18, the catch claw 72 is maintained in the locked state with respect to the axial back edge of the pressing member 14. The protective cap 20 thereby travels forward in the direction of extension of the skin puncture needle 62 with respect to the lancet 18, causing it to separate from the skin puncture needle 62 and causing the spring member 74 to begin to experience compressive deformation.

Figure 11A:
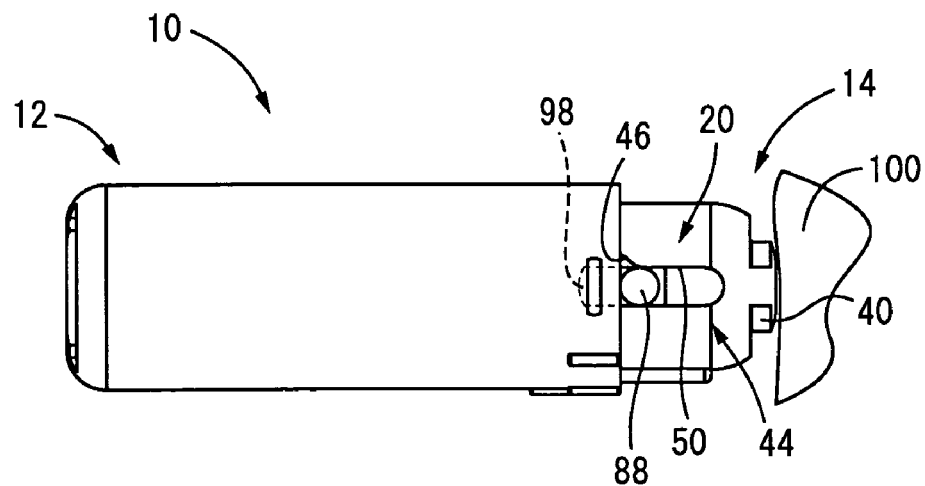
FIGS. 11A and 11B are views for explaining the following step of the skin puncture procedure of FIGS. 10A and 10B, wherein the protective cap is rotated within the housing.
Figure 11B:
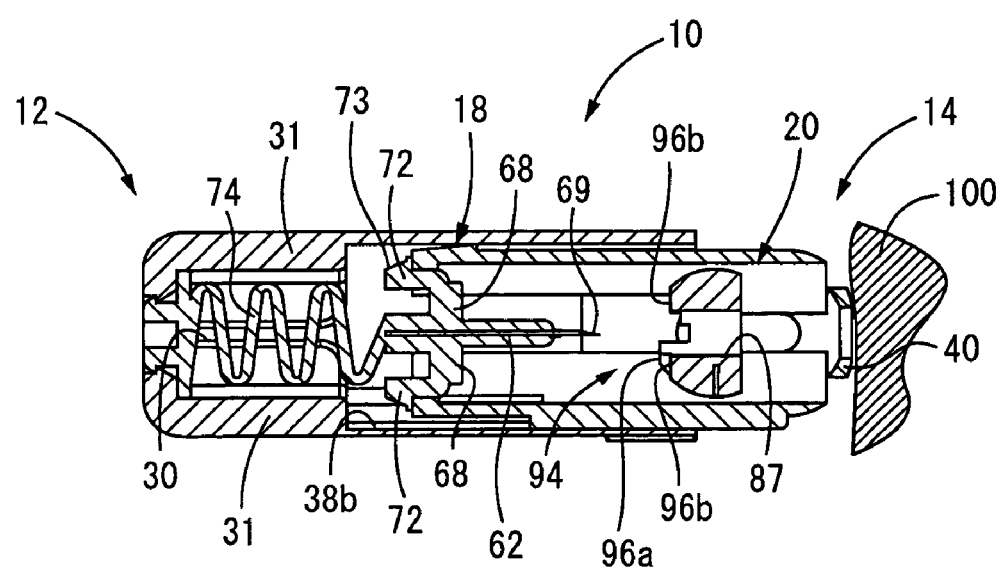

Next, as depicted in FIGS. 11A and 11B, as the operating member 12 continues to be pushed in further, the projecting guide pieces 98 of the protective cap 20 will come into contact against the sloping part 46 of the support grooves 44. The location of the sloping part 46 in the axial direction of the pressing member 14 has been established such that this contact of the projecting guide piece 98 against the sloping part 46 will take place after the protective cap 20 has separated from the skin puncture needle 62. With the projecting guide pieces 98 being guided by the sloping part 46, the support shafts 88 and the projecting guide pieces 98 will rotate about the center axis of the support shafts 88 so as to intrude into the narrow-width part 50, causing the protective cap 20 to rotate by approximately 90° (in FIGS. 9A and 9B, counterclockwise rotation) about the support shafts 88. The needle passage hole 87 will thereby be positioned with its axial direction aligned with the skin puncture needle 62 extension path, while the protective cap 20 will be supported by the pressing member 14 at a location off the skin puncture needle 62 extension path, by virtue of the protective cap 20 being penetrated by the needle passage hole 87 on the skin puncture needle 62 extension path. At the same time, the stopper part 94 will be positioned facing the abutting parts 68 of the lancet 18 in the direction of displacement of the lancet 18.

Here, the abutting parts 68 of the lancet 18 are generally identical in shape to the respective first to third stopper faces 96a, 96b, 96c of the protective cap 20 so as to be positioned in opposition thereto according to the rotational position of the pressing member 14 with respect to the operating member 12. Specifically, with the rib 52 at the position aligned with the first indicia 34a and mated with the first guide groove 38a, the abutting parts 68 of the lancet 18 will be positioned facing the first stopper face 96a in the direction of extension of the skin puncture needle 62. With the rib 52 at the position aligned with the second indicia 34b and mated with the second guide groove 38b, they will be positioned facing the second stopper face 96b. With the rib 52 at the position aligned with the third indicia 34c and mated with the third guide groove 38c, they will be positioned facing the third stopper face 96b. In FIGS. 9A and 9B, by virtue of the rib 52 being aligned with the second indicia 34b, the abutting parts 68 are positioned facing the second stopper face 96b.

The first to third stopper faces 96a, 96b, 96c, depending on their degree of projection, are situated progressively smaller distances away from the abutting parts 68 in the direction of extension of the skin puncture needle 62. In the present embodiment, the distance from the lancet 18 will be smallest when the first stopper face 96a, which has the greatest degree of projection, is positioned facing the abutting parts 68, while the distance from the lancet 18 will be greatest when the third stopper face 96c, which has the smallest degree of projection, is positioned facing the abutting parts 68.

By virtue of the insertion pins 80 passing successively through the insertion grooves 30 of the housing tube portion 26 in association with compressive deformation of the spring member 74, compressive deformation thereof will take place smoothly in the direction of extension of the skin puncture needle 62, and with stable positioning inside the housing 16 during compressive deformation.

As the operating member 12 is pushed farther in, the pressing member 14 will travel farther towards the back in the axial direction of the operating member 12, whereby with the tapered face 73 of the lancet 18 guided by the linking portions 31 of the operating member 12, the catch claw 72 formation zone in the lancet 18 will undergo deformation in the diameter constriction direction. The catch claw 72 of the lancet 18 and the axial back end face of the pressing member 14 will be released from the locked state thereby, the lancet 18 will travel towards the base part 40 of the pressing member 14 due to the elastic recovery force of the spring member 74, and the skin puncture needle 62 will travel forward in the axial direction on the center axis of the housing 16.

Figure 12A:
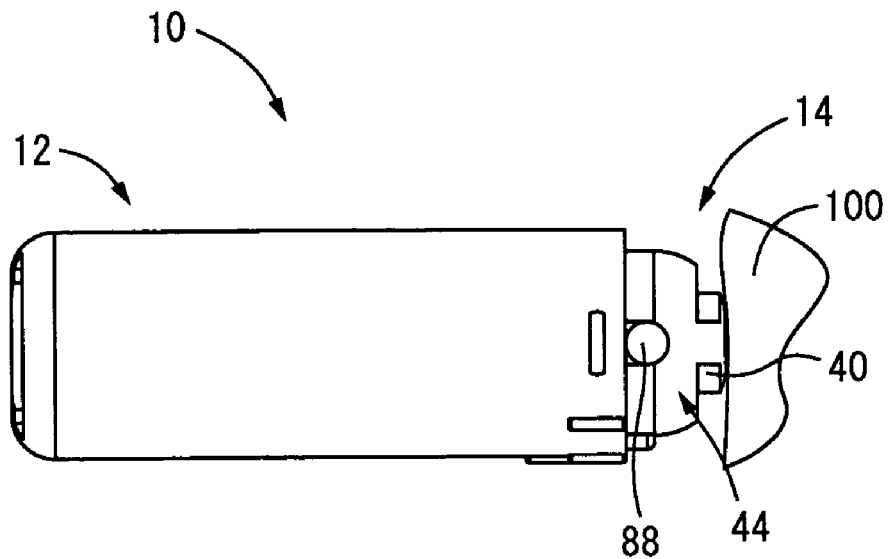
FIGS. 12A and 12B are views for explaining the following step of the skin puncture procedure of FIGS. 11A and 11B, wherein the skin puncture needle punctures the skin surface.
Figure 12B:
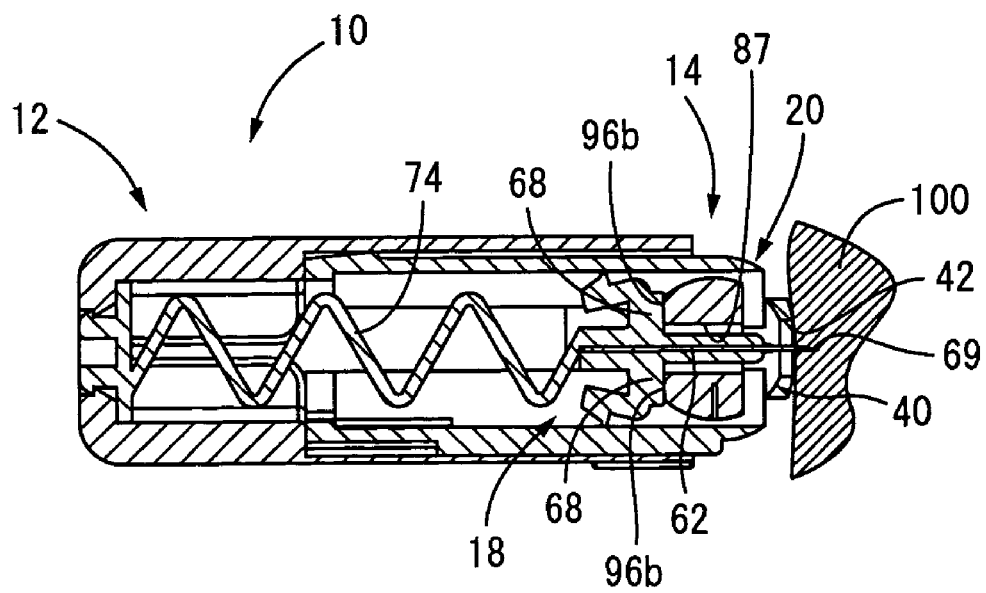

As depicted in FIGS. 12A and 12B, the spring member 74 will momentarily extend beyond its free length through elastic recovery force, and the lancet 18, which was previously urged by the spring member 74, will now be arrested from further forward travel in the axial direction by virtue of the abutting parts 68 coming into abutment against the first, second, or third stopper faces 96a, 96b, 96c, depending on which of these faces they have been positioned facing in the direction of extension of the skin puncture needle 62. The needle tip 69 will thereby be extended out to a prescribed degree from the housing 16 through the needle passage hole 87 of the protective cap 20 and the puncture opening 42 of the pressing member 14, so as to puncture the skin surface 100.

At this point, the degree of extension of the skin puncture needle 62 out from the housing 16, which is regulated by the position of the forward traveling end of the lancet 18, will be established according to the degree of projection of the first to third stopper faces 96a, 96b, 96c, which in the present embodiment is smallest when abutting the first stopper face 96a and greatest when abutting the third stopper face 96c. In FIGS. 9A and 9B, because the abutting parts 68 abut the second stopper face 96b, the degree of extension will be greater than when abutting the first stopper face 96a, but less than when abutting the third stopper face 96c.

Figure 13A:
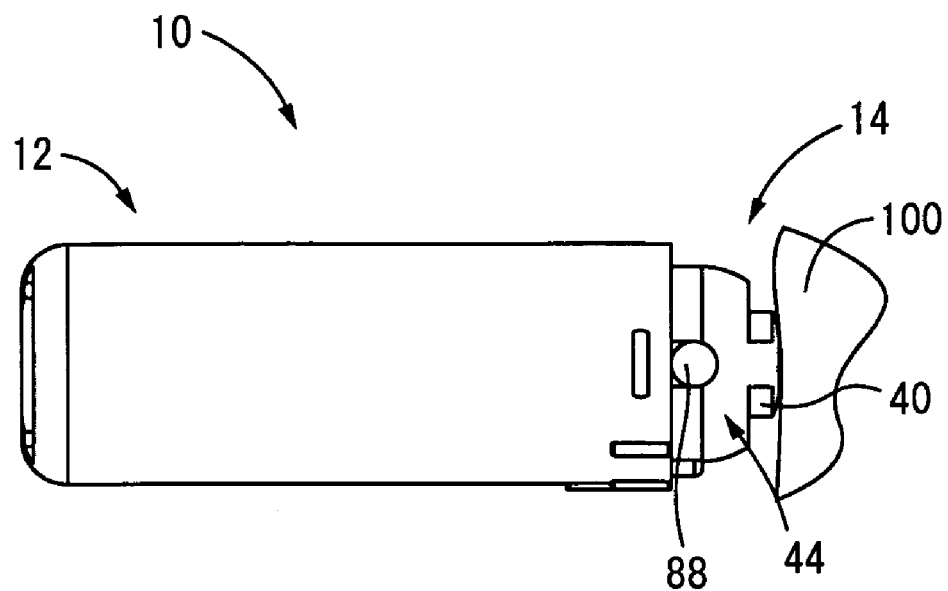
FIGS. 13A and 13B are views for explaining the following step of the skin puncture procedure of FIGS. 12A and 12B, wherein the skin puncture needle is again accommodated inside the housing.
Figure 13B:
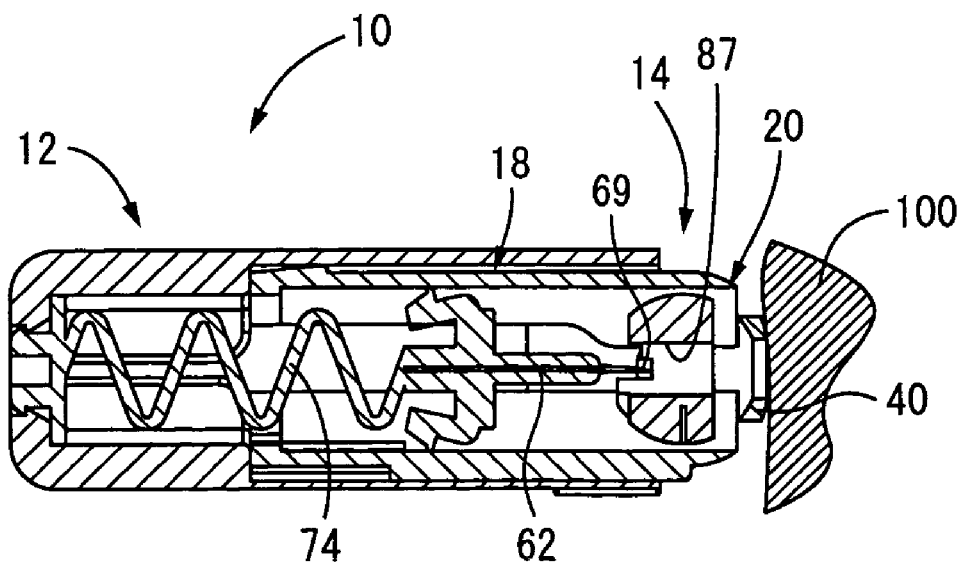

Then, as shown in FIGS. 13A and 13B, the lancet 18 whose forward travel has been arrested by the stopper part 94 will be withdrawn by virtue of the spring member 74 recovering its natural length, whereby the needle tip 69 will again be accommodated inside the housing 16. The needle tip 69 will thereby be prevented from becoming exposed to the outside of the housing 16 and causing an accidental needlestick, as well as making it impossible for the lancing device 10 to be reused, so that the lancing device 10 will be discarded after use.

According to the lancing device 10 having the above construction, by providing the protective cap 20 with the stopper part 94, a protective mechanism for the skin puncture needle 62 and a mechanism for adjusting the degree of extension of the skin puncture needle 62 can be realized through a simple design having few parts. Thus, reduced production costs and smaller size of the lancing device 10 can be achieved.

Further, in the present embodiment, the support shafts 88 and the projecting guide pieces 98 which have been provided to the protective cap 20, the rim face 102 of the operating member 12, the support grooves 44 and sloping parts 46 which have been provided to the pressing member 14 together make up an interlock mechanism adapted to separate the protective cap 20 from the skin puncture needle 62 and position the stopper part 94 in opposition to the lancet 18 in the direction of extension of the skin puncture needle 62, whereby it is possible for these two operations to be carried out automatically through a single operation of pressing the operating member 12 against the skin surface 100, so that better ease of operation can be achieved.

In the present embodiment, by providing the stopper part 94 with a multiple stepped face profile, the degree of extension of the skin puncture needle 62 is adjusted stepwise so that this degree of extension can be set with consistently good accuracy, and enhanced safety may be attained as well. Further, adjustment of the degree of extension of the skin puncture needle 62 is possible through the simple operation of rotating the pressing member 14 with respect to the operating member 12.

While one preferred embodiment of the invention has been described in detail herein, it is to be understood that the description is by way of example only, and the invention should in no way be construed as limited to the details of the illustrated embodiment.

For example, in the preceding embodiment, the stopper part 94 of the protective cap 20 has been designed with a stepped face profile, but in an alternative arrangement, the stopper part 94 will be identical in shape to the abutting parts 68 which have been formed on the lancet hub 60, while the abutting parts 68 on the lancet hub 60 will instead be given a stepped face profile similar to the stopper part 94. During stepwise setting of the degree of extension of the skin puncture needle 62, the number of steps may be established appropriately and may be greater or less than the number taught in the preceding embodiment. Also, by designing the protective cap 20 to move forward and backward steplessly in the direction of extension of the skin puncture needle 62 through screw adjustment for example, it will be possible for the degree of extension of the skin puncture needle 62 to be adjusted steplessly.

In the preceding embodiment, the lancet hub 60 and the spring member 74 have been integrally formed, but it would be possible to form them separately, and to employ as the spring member a plate spring or coil spring of metal or the like. Also, while in the preceding embodiment the spring member 74 has been secured to the operating member 12, it is not essential that the spring member be secured to the operating member 12.

Further, it is not essential to provide an interlock mechanism for releasing the protective cap 20 from the skin puncture needle 62 and leading it to the location for constituting the stopper part 94. It would be possible for example to instead set up the protective cap 20 as the stopper by a manual procedure, after having separated the protective cap 20 from the skin puncture needle 62 by a manual procedure separate from the skin puncture procedure.

What is claimed is:

1. A disposable lancing device comprising:
a housing;
a spring member;
a lancet having a skin puncture needle, the spring member and the lancet being housed within the housing such that a needle tip of the skin puncture needle is adapted to be projected out from the housing under urging of the lancet by the spring member to perform skin puncture procedure; and a protective cap having a needle passage hole and covering the needle tip of the skin puncture needle, the protective cap being adapted to separate from the skin puncture needle and rotate so that the needle passage hole of the protective cap is positioned on a path of projection of the skin puncture needle, and the skin puncture procedure is performed with the protective cap supported on the housing, wherein the protective cap has a cap body in which the needle passage hole is provided, and support shafts provided to the cap body and extending perpendicular to a direction of passage of the needle passage hole; while the housing is provided with support grooves extending in a direction of extension of the skin puncture needle, with the support shafts of the protective cap being supported in the support grooves of the housing.

2. The disposable lancing device according to claim 1, wherein each of the support shafts of the protective cap is provided with a projecting guide piece that extends in the direction of passage of the needle passage hole; each of the support grooves of the housing has a wide-width part, a narrow-width part, and a sloping part that connects the wide-width part with the narrow-width part; and the protective cap is adapted to be rotated by sliding the projecting guide pieces into the support grooves and movement thereof from a wide-width part end towards a narrow-width part end.

3. The disposable lancing device according to claim 1, wherein during the skin puncture procedure, the protective cap separated from the skin puncture needle defines a stopper part against which the lancet comes into abutment; and a degree of projection of the skin puncture needle beyond the housing is adjustable through modification of a position of a traveling end of the lancet in a direction of projection of the skin puncture needle, which is regulated by abutment of the lancet against the stopper part.

4. The disposable lancing device according to claim 1, wherein the housing includes a pressing member adapted to be pressed against a skin surface at a blood collection site, and an operating member moveably linked to the pressing member; and the operating member is movable to release a locked state of the lancet urged by the spring member with respect to the pressing member so that the skin puncture needle is projected out from the pressing member to carry out the skin puncture procedure.

5. The disposable lancing device according to claim 4, wherein both the pressing member and the operating member are of tubular shape having a bottom, and are oriented with openings thereof fitting together and assembled so as to be capable of relative movement in an axial direction to produce a hollow structure for the housing; the lancet is accommodated in the housing so as to be moveable in the axial direction thereof, with the skin puncture needle of the lancet projecting towards a base part of the pressing member and with a puncture opening formed in the base part of the pressing member; the protective cap is designed to separate from the skin puncture needle and to rotate through push operation of the operating member against the pressing member with the base part of the pressing member being pressed against the skin surface at the blood collection site; and the skin puncture procedure is carried out by releasing the lancet from the locked state with respect to the pressing member, whereupon the lancet moves towards the base part of the pressing member under urging force of the spring member situated between the housing and the lancet, causing the needle tip of the skin puncture needle to project to an outside through the puncture opening of the pressing member to carry out the skin puncture procedure.

6. The disposable lancing device according to claim 4, wherein the operating member is furnished with a safety lock mechanism adapted to arrest operation for releasing the locked state of the lancet urged by the spring member with respect to the pressing member.

7. The disposable lancing device according to claim 4, wherein when the protective cap which is supported by the pressing member and the lancet which is supported by the operating member experience relative rotation through coaxial relative rotation of the pressing member with respect to the operating member, a location at which the lancet comes into abutment with a stopper part formed on the protective cap changes so as to produce an associated change in a position of a traveling end of the lancet which is regulated by abutment thereof against the stopper part.

8. The disposable lancing device according to claim 3, wherein a position of an abutting face of the stopper part which abuts the lancet is changeable in the direction of projection of the skin puncture needle.

9. The disposable lancing device according to claim 4, further comprising an interlock mechanism whereby operating force exerted on the operating member during the skin puncture procedure is transmitted to the protective cap so that the protective cap is induced to separate from the skin puncture needle and is guided to a location for constituting a stopper part.

* * * * *